(12) United States Patent
Gonzalez-Hernandez

(10) Patent No.: US 8,361,075 B2
(45) Date of Patent: Jan. 29, 2013

(54) METHOD FOR REPAIRING FRACTURED BONE

(75) Inventor: Eduardo Gonzalez-Hernandez, Coconut Grove, FL (US)

(73) Assignee: Toby Orthopaedics, Inc., Miami, FL (US)

(*) Notice: Subject to any disclaimer, the term of this patent is extended or adjusted under 35 U.S.C. 154(b) by 0 days.

(21) Appl. No.: 12/803,394

(22) Filed: Jun. 25, 2010

(65) Prior Publication Data

US 2010/0274245 A1 Oct. 28, 2010

Related U.S. Application Data

(60) Division of application No. 11/050,304, filed on Feb. 3, 2005, now Pat. No. 8,182,485, which is a continuation of application No. 10/993,723, filed on Nov. 19, 2004, now abandoned.

(60) Provisional application No. 60/552,632, filed on Mar. 12, 2004, provisional application No. 60/541,540, filed on Feb. 3, 2004, provisional application No. 60/523,960, filed on Nov. 21, 2003.

(51) Int. Cl.
*A61B 17/56* (2006.01)

(52) U.S. Cl. ............... 606/71; 606/62; 606/281

(58) Field of Classification Search ............ 606/62–67, 606/96, 98, 300–310
See application file for complete search history.

(56) References Cited

U.S. PATENT DOCUMENTS

| | | | |
|---|---|---|---|
| 2,500,370 A | 3/1950 | McKibbin | |
| 3,489,143 A | 1/1970 | Halloran | |
| 3,552,389 A | 1/1971 | Allgower et al. | |
| 3,579,831 A | 5/1971 | Stevens et al. | |
| 3,716,050 A | 2/1973 | Johnston | |
| 3,791,380 A | 2/1974 | Dawidowski | |
| 3,900,025 A | 8/1975 | Barnes, Jr. | |
| 4,535,768 A | 8/1985 | Hourahane et al. | |
| 4,683,878 A | 8/1987 | Carter | |
| 4,733,654 A * | 3/1988 | Marino ..................... 606/64 |
| 4,776,330 A | 10/1988 | Chapman et al. | |
| 4,790,302 A | 12/1988 | Colwill et al. | |
| 4,794,919 A | 1/1989 | Nilsson | |
| 4,838,264 A | 6/1989 | Bremer et al. | |
| 4,858,602 A | 8/1989 | Seidel et al. | |
| 4,870,957 A | 10/1989 | Goble et al. | |

(Continued)

FOREIGN PATENT DOCUMENTS

| | | |
|---|---|---|
| DE | 86 28 766 U1 | 12/1986 |
| DE | 89 07 443 U1 | 9/1989 |

(Continued)

OTHER PUBLICATIONS

U.S. Appl. No. 10/993,723, filed Nov. 2004, Gonzalez-Hernandez.

(Continued)

*Primary Examiner* — Eduardo C. Robert
*Assistant Examiner* — Tara Carter
(74) *Attorney, Agent, or Firm* — Martin & Ferraro, LLP

(57) ABSTRACT

A method for repairing a fractured bone includes providing a bone fracture fixation assembly including a plate, an elongated shaft, and a rod. At least a portion of the shaft is threaded, and the shaft has a hole extending therethrough. The hole has an axis transverse to a longitudinal axis of the shaft. The method further includes positioning the plate adjacent the surface of the fractured bone, extending the shaft into the bone, cooperatively engaging the threaded portion of the shaft with a screw receiving aperture of the plate, extending the rod into the bone, and inserting the rod into the hole of the shaft.

15 Claims, 8 Drawing Sheets

U.S. PATENT DOCUMENTS

| | | | |
|---|---|---|---|
| 5,003,969 A | 4/1991 | Azer et al. |
| 5,041,114 A | 8/1991 | Chapman et al. |
| 5,180,383 A | 1/1993 | Haydon |
| 5,190,544 A | 3/1993 | Chapman et al. |
| 5,324,291 A | 6/1994 | Ries et al. |
| 5,356,410 A | 10/1994 | Pennig |
| 5,364,399 A | 11/1994 | Lowery et al. |
| 5,423,860 A | 6/1995 | Lizardi et al. |
| 5,437,667 A | 8/1995 | Papierski et al. |
| 5,458,654 A | 10/1995 | Tepic |
| 5,462,547 A | 10/1995 | Weigum |
| 5,472,444 A | 12/1995 | Huebner et al. |
| 5,505,734 A | 4/1996 | Caniggia et al. |
| 5,578,035 A | 11/1996 | Lin |
| 5,584,835 A | 12/1996 | Greenfield |
| 5,586,985 A | 12/1996 | Putnam et al. |
| 5,601,553 A | 2/1997 | Trebing et al. |
| 5,620,449 A | 4/1997 | Faccioli et al. |
| 5,658,287 A | 8/1997 | Hofmann et al. |
| 5,665,088 A | 9/1997 | Gil et al. |
| 5,674,222 A | 10/1997 | Berger et al. |
| 5,676,667 A | 10/1997 | Hausman |
| 5,681,311 A | 10/1997 | Foley et al. |
| 5,709,686 A | 1/1998 | Talos et al. |
| 5,749,872 A | 5/1998 | Kyle et al. |
| 5,766,174 A | 6/1998 | Perry |
| 5,776,194 A | 7/1998 | Mikol et al. |
| 5,779,704 A | 7/1998 | Kim |
| 5,785,712 A | 7/1998 | Runciman et al. |
| 5,840,078 A | 11/1998 | Yerys |
| 5,868,749 A | 2/1999 | Reed |
| 5,931,839 A | 8/1999 | Medoff |
| 5,976,139 A | 11/1999 | Bramlet |
| 6,030,389 A | 2/2000 | Wagner et al. |
| 6,096,040 A | 8/2000 | Esser |
| 6,149,653 A | 11/2000 | Deslauriers |
| 6,152,927 A | 11/2000 | Farris et al. |
| 6,200,330 B1 | 3/2001 | Benderev et al. |
| 6,206,881 B1 | 3/2001 | Frigg et al. |
| D443,060 S | 5/2001 | Benirschke et al. |
| 6,270,499 B1 | 8/2001 | Leu et al. |
| 6,331,179 B1 | 12/2001 | Freid et al. |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,379,359 B1 | 4/2002 | Dahners |
| 6,398,783 B1 | 6/2002 | Michelson |
| 6,406,478 B1 | 6/2002 | Kuo |
| 6,409,768 B1 | 6/2002 | Tepic et al. |
| 6,413,259 B1 | 7/2002 | Lyons et al. |
| 6,440,135 B2 | 8/2002 | Orbay et al. |
| 6,468,278 B1 | 10/2002 | Muckter |
| 6,572,620 B1 | 6/2003 | Schon et al. |
| 6,620,195 B2 | 9/2003 | Goble et al. |
| 6,623,486 B1 | 9/2003 | Weaver et al. |
| 6,663,669 B1 | 12/2003 | Reiley |
| 6,669,701 B2 | 12/2003 | Steiner et al. |
| 6,695,844 B2 | 2/2004 | Bramlet et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,866,665 B2 | 3/2005 | Orbay |
| 6,916,323 B2 | 7/2005 | Kitchens |
| 6,945,973 B2 | 9/2005 | Bray |
| 7,001,388 B2 | 2/2006 | Orbay et al. |
| 7,128,744 B2 | 10/2006 | Weaver et al. |
| D536,453 S | 2/2007 | Young et al. |
| 7,220,246 B2 | 5/2007 | Raulerson |
| 7,229,445 B2 | 6/2007 | Hayeck et al. |
| 7,235,079 B2 | 6/2007 | Jensen et al. |
| 7,354,441 B2 | 4/2008 | Frigg |
| 7,500,983 B1 | 3/2009 | Kaiser et al. |
| 7,563,263 B2 | 7/2009 | Orbay et al. |
| 7,582,107 B2 | 9/2009 | Trail et al. |
| 7,591,823 B2 | 9/2009 | Tipirneni |
| 7,637,908 B1 | 12/2009 | Gonzalez-Hernandez |
| 7,651,517 B2 | 1/2010 | Konieczynski et al. |
| 7,655,029 B2 | 2/2010 | Niederberger et al. |
| 7,695,472 B2 | 4/2010 | Young |
| 7,722,653 B2 | 5/2010 | Young et al. |
| 7,740,648 B2 | 6/2010 | Young et al. |
| 7,744,638 B2 | 6/2010 | Orbay |
| 7,776,076 B2 | 8/2010 | Grady, Jr. et al. |
| 7,780,667 B2 | 8/2010 | Watanabe et al. |
| 7,780,710 B2 | 8/2010 | Orbay et al. |
| 7,909,859 B2 | 3/2011 | Mosca et al. |
| 8,182,485 B1 | 5/2012 | Gonzalez-Hernandez |
| 2002/0143337 A1 | 10/2002 | Orbay et al. |
| 2003/0135216 A1 | 7/2003 | Sevrain |
| 2004/0193278 A1 | 9/2004 | Maroney et al. |
| 2005/0004574 A1 | 1/2005 | Muckter |
| 2005/0010226 A1 | 1/2005 | Grady et al. |
| 2005/0015089 A1 | 1/2005 | Young et al. |
| 2005/0267476 A1 | 12/2005 | Chervitz et al. |
| 2005/0288681 A1 | 12/2005 | Klotz et al. |
| 2006/0015072 A1 | 1/2006 | Raulerson |
| 2006/0015101 A1 | 1/2006 | Warburton et al. |
| 2006/0161156 A1 | 7/2006 | Orbay |
| 2006/0235400 A1 | 10/2006 | Schneider |
| 2007/0005074 A1 | 1/2007 | Chudik |
| 2007/0162015 A1 | 7/2007 | Winquist et al. |
| 2008/0045960 A1 | 2/2008 | Bruecker et al. |
| 2008/0132955 A1 | 6/2008 | Frigg |
| 2008/0140130 A1 | 6/2008 | Chan et al. |
| 2009/0228010 A1 | 9/2009 | Gonzalez-Hernandez et al. |
| 2009/0312760 A1 | 12/2009 | Forstein et al. |
| 2010/0145339 A1 | 6/2010 | Steffen |
| 2011/0152943 A1 | 6/2011 | Gonzalez-Hernandez |
| 2012/0083848 A1 | 4/2012 | Gonzalez-Hernandez |
| 2012/0109322 A1 | 5/2012 | Gonzalez-Hernandez |
| 2012/0197305 A1 | 8/2012 | Gonzalez-Hernandez |
| 2012/0197308 A1 | 8/2012 | Gonzalez-Hernandez |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| FR | 2 606 268 A1 | 5/1988 |
| FR | 2 680 673 A1 | 3/1993 |
| JP | 4-138152 A | 5/1992 |
| WO | WO 2005/037117 | 4/2005 |
| WO | WO 2008/007194 A2 | 1/2008 |

OTHER PUBLICATIONS

U.S. Appl. No. 11/050,304, filed Feb. 2005, Gonzalez-Hernandez.
U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.
U.S. Appl. No. 11/707,775, filed Feb. 2007, Gonzalez-Hernandez.
U.S. Appl. No. 13/253,564, filed Oct. 2011, Gonzalez-Hernandez.
U.S. Appl. No. 13/282,810, filed Oct. 2011, Gonzalez-Hernandez.
Acumed; The Mayo Clinic Congruent Elbow Plates (cataiog); 2003; 19 pages.
Christie, J., C.R. Howie and P.C. Armour, Fixation of displaced subcapital femoral fractures. Compression screw fixation versus double divergent pins.*J Bone Joint Surd* [Br] 1988; 70-B: 199-201.
Guha, AR, et ai.; "A New Technique of Fixation of Radial Head Fractures Using a Modified Tubular Plate," Journal of Postgraduate Medicine; Jul. 2004; vol, 50, issue 2; pp. 113-114; Accessed Aug. 6, 2008 at: http://www.jpgmonline.corn/articie.asp?issn=0022- 3859: year=2004;voiume=50;issue=2;spage=113;epage=114;aulast= Guha.
Robert, III, K.Q., R. Chandler, R,V, Barratta, K.A. Thomas and M.B. Harris, The effect of divergent screw placement on the initial strength of plate-to-bone fixation.*J. Trauma*. Dec. 2003;55(6):1139-44.
SYNTHES; Locking Compression Plate (LCP) System (brochure); 2003; 6 pages.

Written Opinion of the International Searching Authority; International Application No,: PCT/US2009/036211; Sep. 23, 2010; 8 pages.

ZIMMER; Zimmer Periarticular Plating System-Low-Profile Fixation (catalog); 2003; 8 pages.

"MIS Technique," published by Zimmer®, 1 page, prior to Nov. 19, 2004.

Postak, Paul D.; "Biomechanical Properties of Fixed-Angie Volar Distal Radius Plates Under Dynamic Loading;" 2007; 6 pages.

Synthes, "Large Fragment LCP instrument and Implant Set;" technique guide; 2003; 31 pages.

Synthes, "Locking Compression Plate (LCP) System. Locking screw technology and conventional plating in one system;" 2003; 6 pages.

SYNTHES; Modular Mini Fragment LCP System (brochure); 2007; 12 pages.

SYNTHES; Small Fragment Locking Compression Plate (LCP) System (brochure); 2002; 43 pages.

* cited by examiner

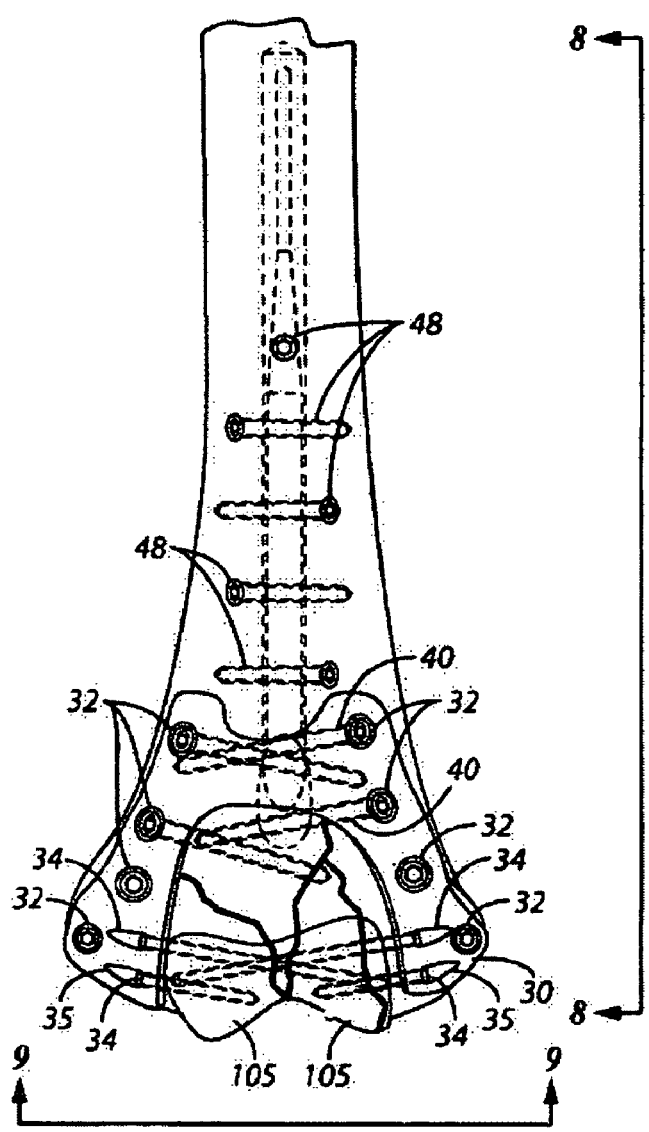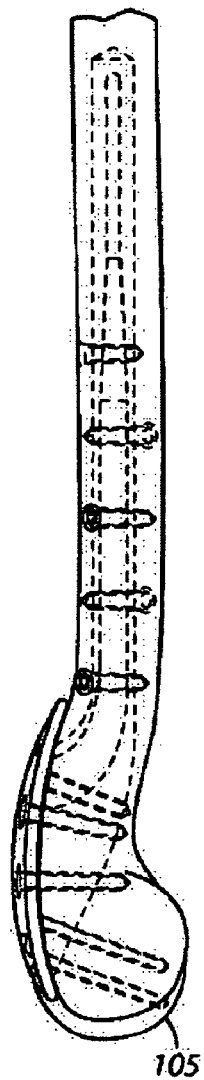
FIG. 7  FIG. 8
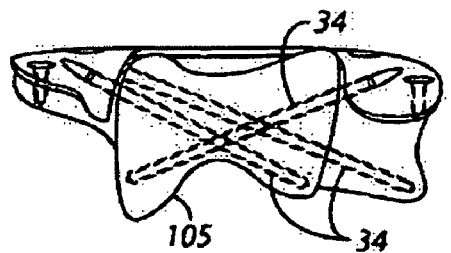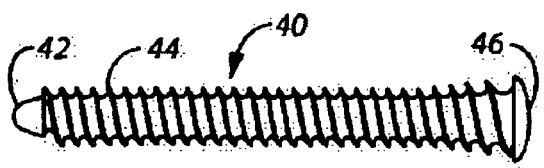
FIG. 9  FIG. 10

METHOD FOR REPAIRING FRACTURED BONE

CROSS-REFERENCE TO RELATED APPLICATIONS

This application is a divisional application of U.S. patent application Ser. No. 11/050,304, filed Feb. 3, 2005 now U.S. Pat. No. 8,182,485; which is a continuing application of U.S. Non-Provisional Patent Application No. 10/993,723, filed on Nov. 19, 2004 (now abandoned); which claims the benefit of Provisional Patent Application No. 60/552,632, filed on Mar. 12, 2004; Provisional Patent Application No. 60/541,540, filed on Feb. 3, 2004; and Provisional Patent Application No. 60/523,960, filed on Nov. 21, 2003; all of which are incorporated herein by reference.

BACKGROUND OF THE INVENTION

1. Field of the Invention

The present invention relates generally to medical devices configured towards the treatment of bone fractures, and more particularly, to a multi-faceted bone fixation system configured towards treating a variety of different human bone fractures.

2. Description of the Prior Art

A wide variety of devices have been developed for the support and treatment of different bone fractures. Existing solutions have ranged from simplistic measures, such as bone support plates, structural rods, and other single-function prosthetic devices, to more elaborate mechanisms involving a complex arrangement of different components.

Although a variety of different approaches have been attempted in the past, existing solutions have consisted basically of familiar, expected, and obvious structural configurations that have proven to be inadequate or impractical in application.

In this respect, there is a need in the art for an efficient and effective fracture fixation system that substantially departs from the prior art, and in so doing, provides a fracture fixation system oriented towards providing significant initial structural integrity as well as rapid patient recovery.

SUMMARY OF THE INVENTION

The present invention is directed to a bone fixation system including a plate portion and a rod portion configured for significant initial structural integrity and rapid patient recovery.

An object of the present invention is to provide a fracture fixation system configured to offer substantial initial structural integrity in the proximity of a bone fracture.

A further object of the present invention is to provide a fracture fixation system incorporating a plurality of screws configured and placed so as to maximize imbedded screw depth into bone structure having the greatest density.

Another object of the present invention is to provide a fracture fixation system utilizing a plurality of screws configured specifically for a rigid and tight hold resistant to free play and loosening.

An additional object of the present invention is to provide a fracture fixation system utilizing fasteners configured for divergent angle placement in order to provide increased structural load resistance.

A further object of the present invention is to provide a fracture fixation system configured for strategic placement in any of a wide variety of bone fracture applications.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 7 is a rear view of the fractured humerus bone shown after complete securement of the rod and plate portion of the fracture fixation system in accordance with an exemplary embodiment of the present invention;

FIG. 8 is a side view of the fractured humerus bone shown after complete securement of the rod and plate portion of the fracture fixation system in accordance with an exemplary embodiment of the present invention;

FIG. 9 is a bottom view of the fractured humerus bone shown after complete securement of the rod and plate portion of the fracture fixation system in accordance with an exemplary embodiment of the present invention;

FIG. 10 is a front view showing an illustrative screw configuration utilized in conjunction with an exemplary embodiment of the present invention;

Like reference numerals refer to like parts throughout the several views of the drawings.

DETAILED DESCRIPTION OF THE PREFERRED EMBODIMENTS

Shown throughout the figures, the present invention is generally directed to a fracture fixation system configured towards treating a variety of different human bone fractures.

Figure 1:
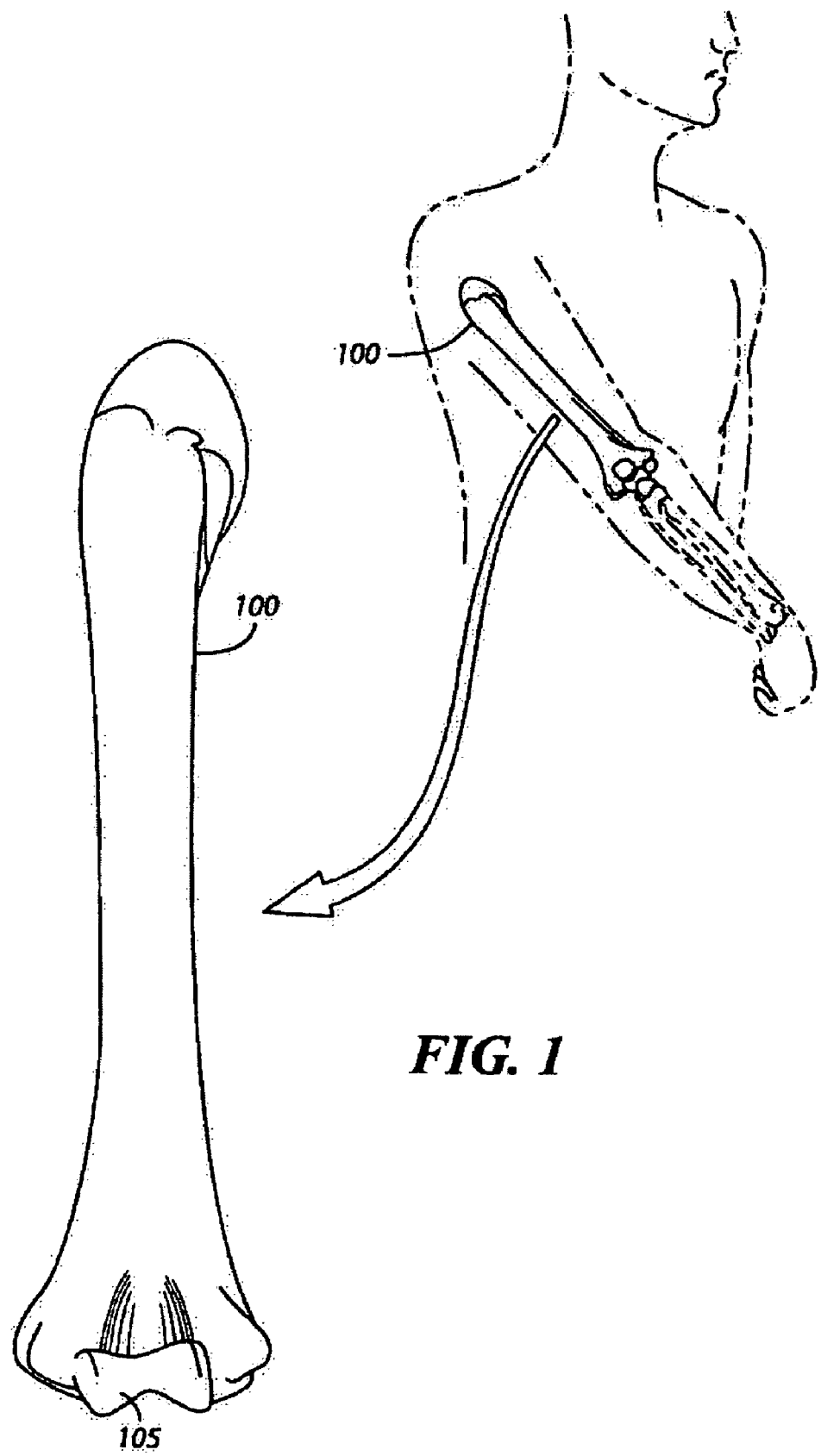
FIG. 1 is a rear view of a humerus bone as located in the human skeletal system.

For purposes of clarity and simplicity, the fracture fixation system of the present invention will be described and illustrated in conjunction with a fractured humerus bone 100. As such, FIG. 1 depicts a rear view of the humerus bone 100 alongside a human figure for perspective. It will be appreciated by those skilled in the art, however, that the fracture fixation system is by no means limited to the support and treatment of the humerus bone 100 and may be adapted to any of a wide variety of other situations without departing from the present invention.

Figure 2:
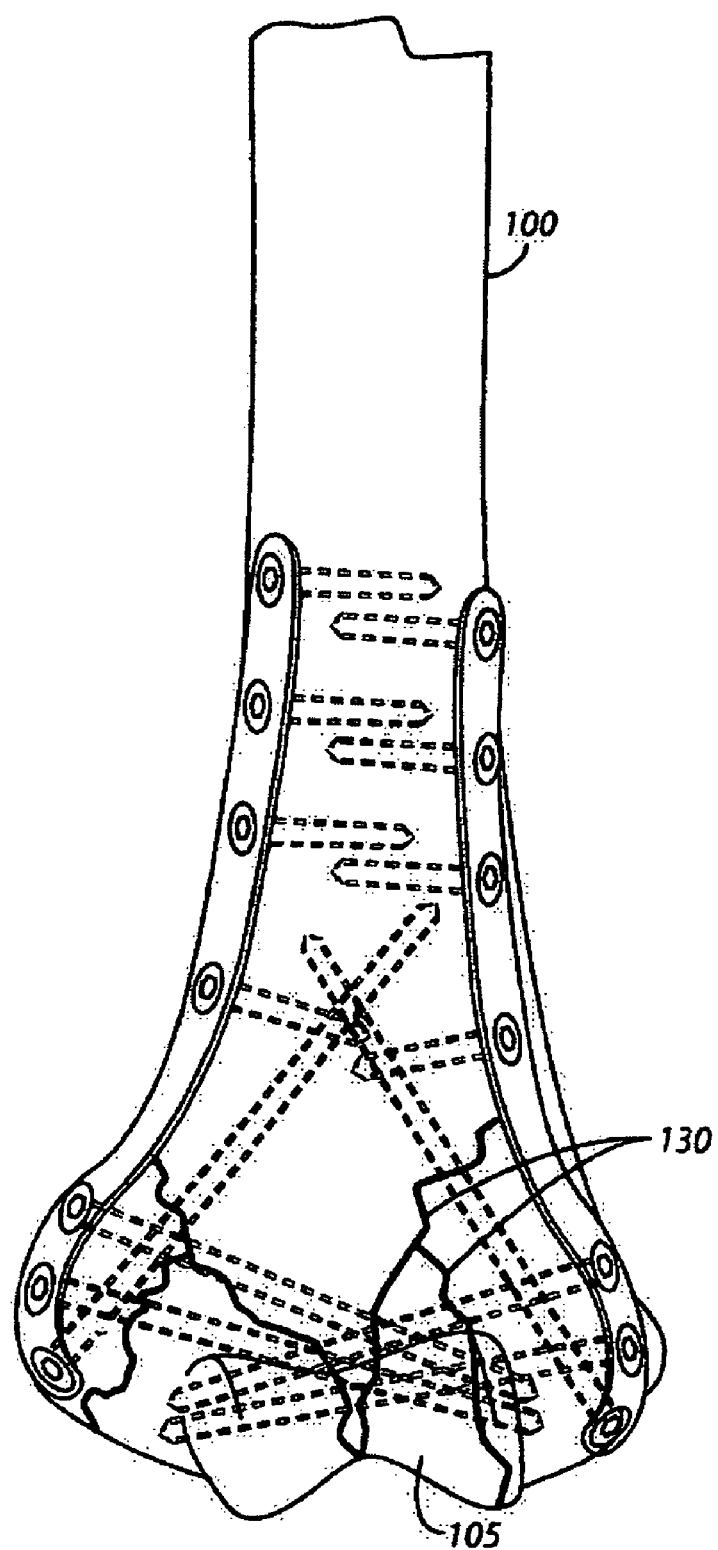
FIG. 2 is a rear view of a fractured humerus bone shown in conjunction with plates and screws as typically utilized in the prior art.

FIG. 2 shows a fractured humerus bone 100 in conjunction with a typical prior art plate and screw support structure. In this figure, it is seen that the humerus bone 100 has multiple fracture lines 130 in the distal end 140 and is supported externally through separate plate components without any internal support mechanism.

Figures 3, 4:
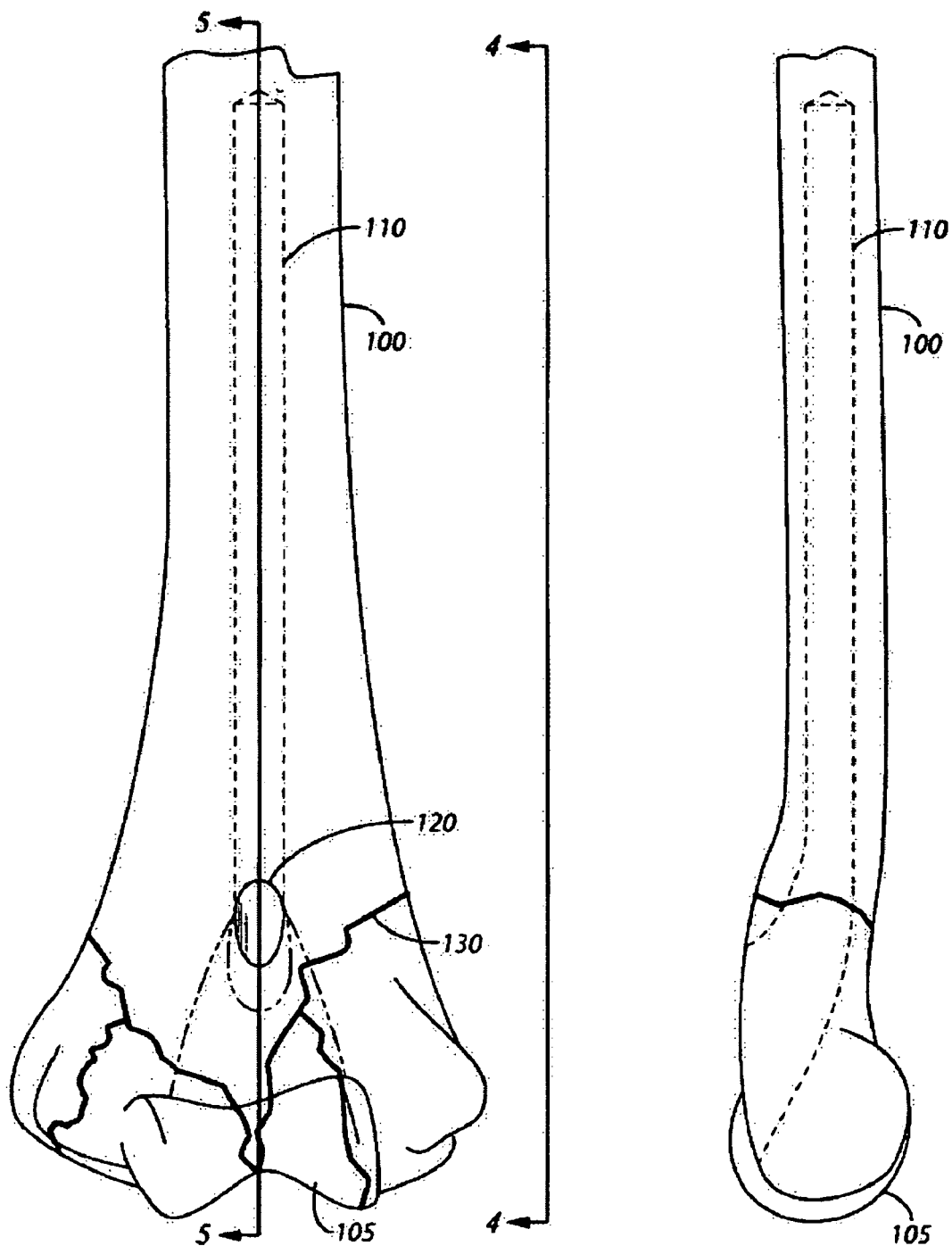
FIG. 3 is a rear view showing a fractured humerus bone showing an aperture drilled axially therein for placement of a rod in accordance with an exemplary embodiment of the present invention.
FIG. 4 is a side view of the fractured humerus bone of FIG. 3 showing the axially drilled aperture in accordance with an exemplary embodiment of the present invention.

Turning to the present invention, FIGS. 3-11 illustrate the fracture fixation system 10 in various stages of completion. Initially, as indicated by the phantom lines of FIG. 3, access to the medullary cavity 110 is achieved by drilling axially from an insertion point 120 at the distal end 140 of the humerus bone 100 as indicated by the phantom lines shown. It will be appreciated by those skilled in the art that any of a wide variety of known methods may be utilized to create access to the medullary cavity 110 without departing from the present invention. FIG. 4 shows a side view of the humerus bone 100 along with the medullary cavity 110 illustrated in phantom lines.

Figures 5, 6:
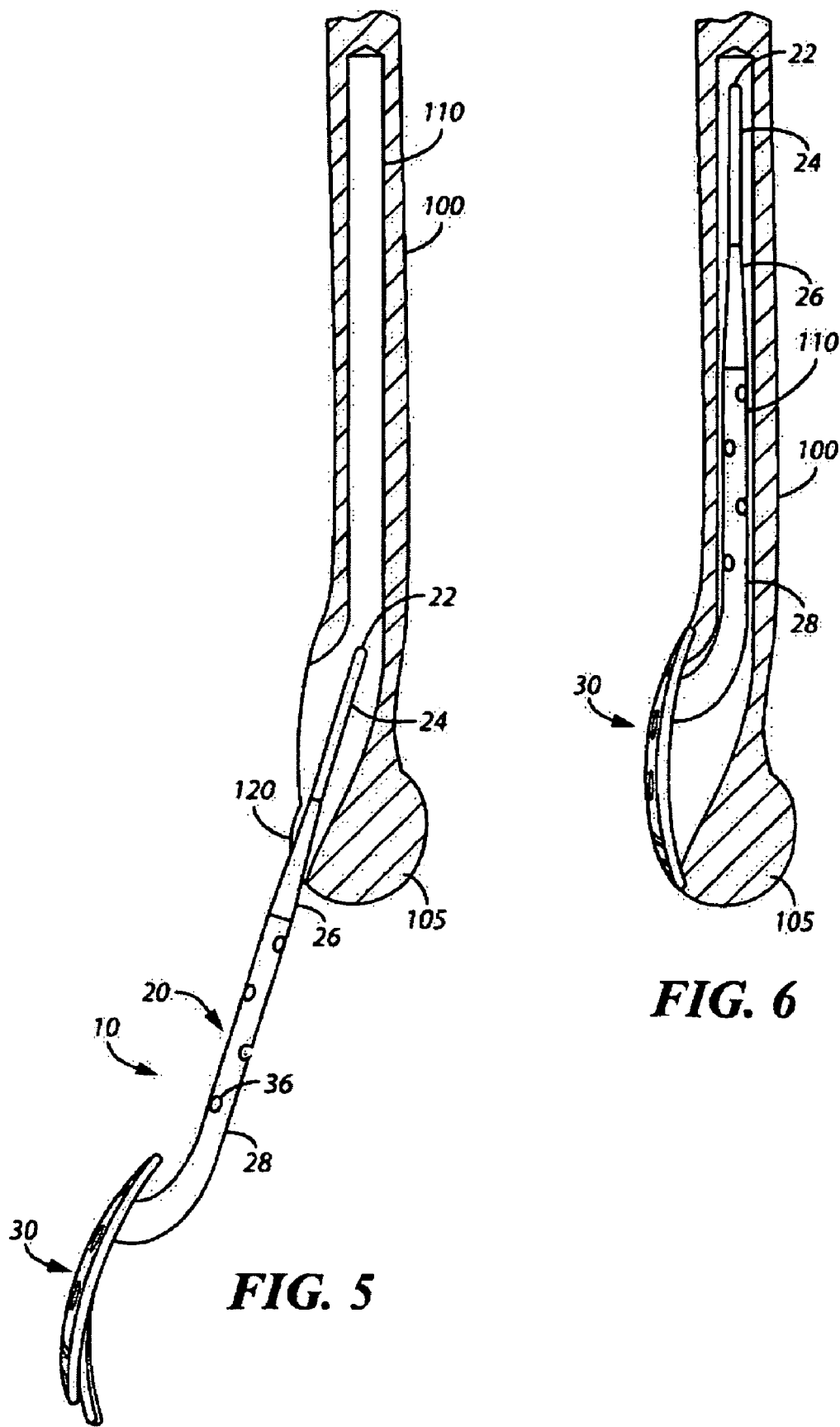
FIG. 5 is a side view of the fractured humerus bone shown before insertion of the rod and plate portion of the fracture fixation system in accordance with an exemplary embodiment of the present invention.
FIG. 6 is a side view of the fractured humerus bone shown after insertion of the rod and plate portion of the fracture fixation system in accordance with an exemplary embodiment of the present invention.

The fracture fixation system 10 is illustrated before insertion into a fractured humerus bone in FIG. 5. The fracture fixation system 10 of the present invention includes a rod portion 20 and a plate portion 30 as shown. The rod portion preferably includes a tip 22, a tip portion 24, tapered central portion 26, and a generally curved plate abutting portion 28. As illustrated in FIG. 6, the plate portion 30 is configured to abut the distal end 140 of the humerus bone 100 in a secure and snug fashion when in a fully inserted position. As shown, the plate portion 30 will include a plurality of apertures 32 therein configured to permit entry of screws 40 there thru and into bone structure 100. The screws 40 are shown in a fully inserted position in the fracture fixation system of the present invention in FIGS. 7-9.

The apertures 32 in the plate portion 30 will preferably be configured such that the central axes of the screws are not parallel to each other. In a most preferred embodiment, each screw 40 will be maintained such that its central axis is not parallel to the central axis of any other screw 40. Such an orientation significantly increases the structural integrity of the fracture fixation system and helps prevent the plate portion from coming loose during loading conditions. Cartilage bearing bone 105 is always weakest in its central portion where it is soft, spongy trabecular bone. The mechanical quality of the cartilage bearing bone 105 is much better just below the cartilage itself, where it is known by the name of subchondral bone. A plurality of pins 34 will be utilized as shown. The pins 34 extend through apertures 35 in a manner configured to maximize the depth that is embedded into high density bone, and likewise, minimize embedded depth into weak bone. The orientation of the pins 34 is as tangential as possible to the articular surface to achieve the best purchase into the hard subchondral bone.

Referring now to FIG. 10, an exemplary embodiment of the front view of the screw 40 is shown. As illustrated, the screw 40 will be generally cylindrical in shape extending from an initial point 42 to a terminal end 46 and include thread 44 on an outer circumference thereupon. In a most preferred embodiment, the thread 42 will extend all the way up to the terminal 46 of the screw 40. As the threading continues up to the terminal end 46 of the screw 40, it is seen that a tight and secure connection is formed. Threading the screw 40 up to and including the terminal end 46 helps prevent any lateral displacement of the terminal end 46 of the screw 40. In the preferred embodiment, the apertures 32 in the plate portion 30 will be internally threaded to matingly correspond to the threads 44 of screws 40.

The pins 34 of the fracture fixation system 10 may be configured similar to the screws 40 in that they may be threaded to matingly correspond to internal threads of apertures 35. As will be clear to those skilled in the art, a wide variety of known pin and screw configurations may be alternatively utilized without departing from the present invention.

As previously described, the fracture fixation system 10 includes a rod portion 20 and a plate portion 30 as best illustrated in FIGS. 5-8. The rod portion 20 is formed in an elongate conical configuration having a tip 22, a tip portion 24, tapered central portion 26, and a generally curved plate abutting portion 28. The generally curved plate abutting portion 28 includes a plurality of apertures 36 therein as shown. The apertures 36 of the plate abutting portion 28 are configured to receive a screw 48 therein as depicted in FIGS. 7-8.

Figure 11:
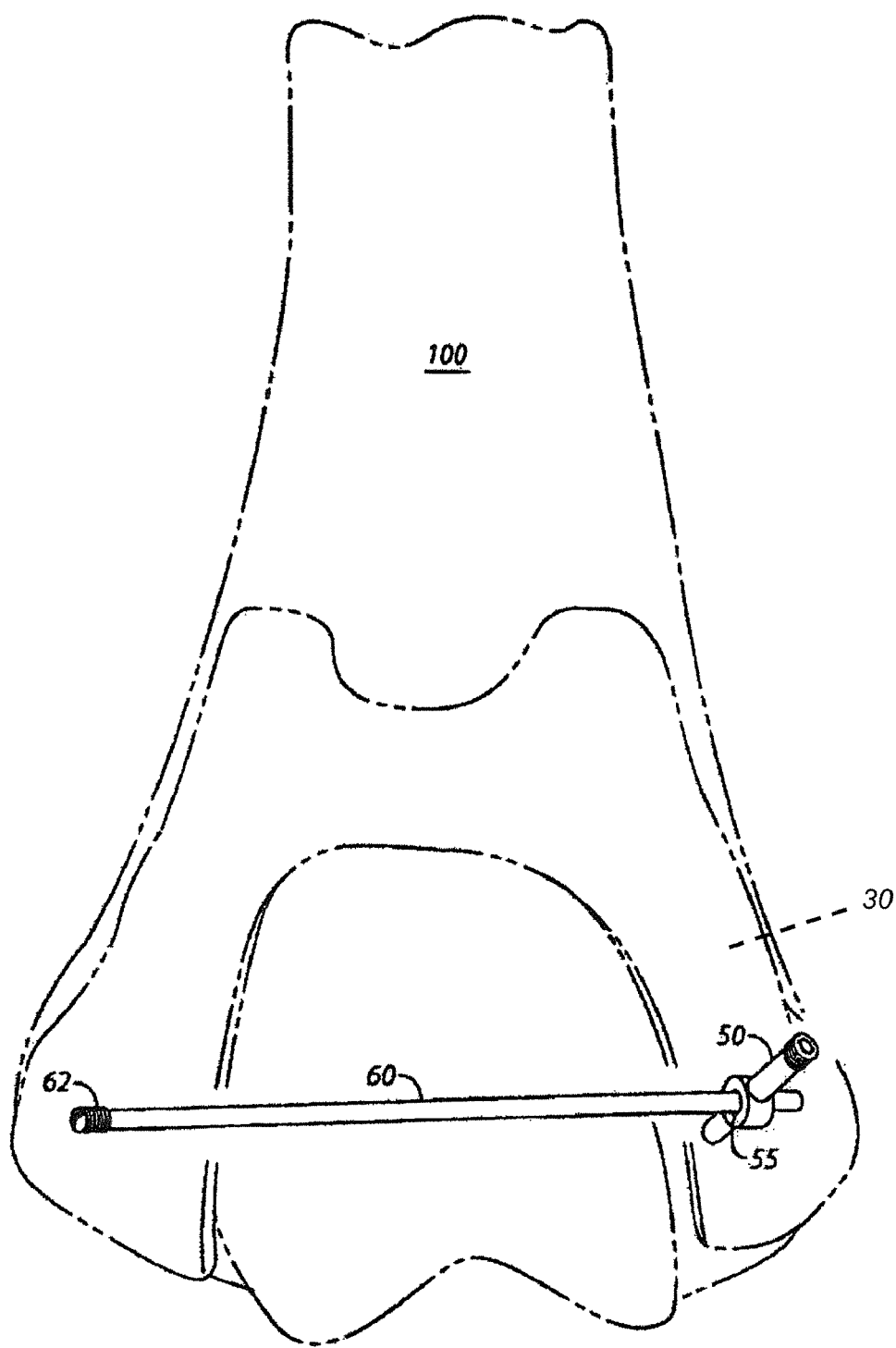
FIG. 11 is a rear view of the humerus bone shown in conjunction with a bone scaffolding system in accordance with an alternative embodiment of the present invention.
Figure 11A:
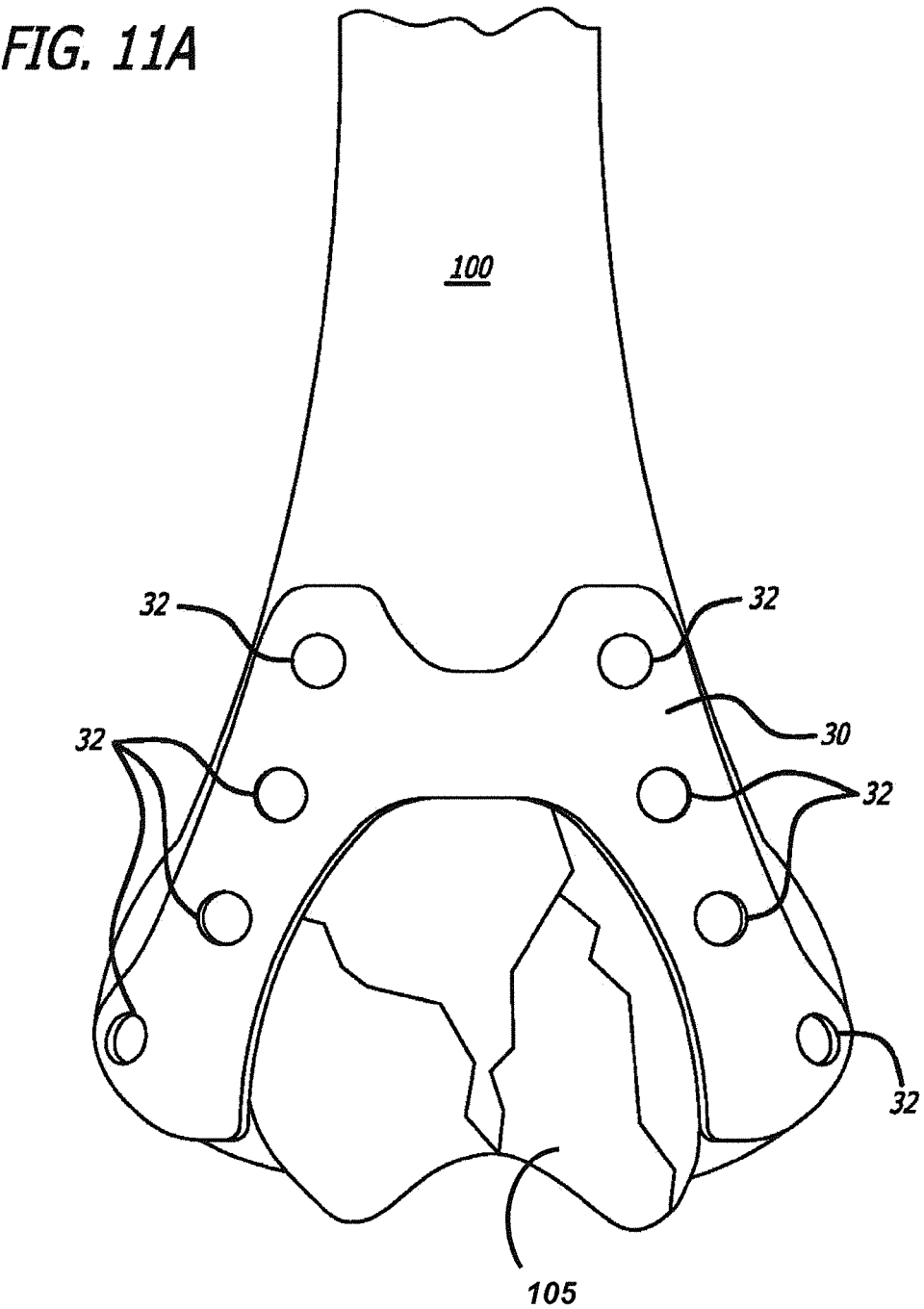
FIG. 11A is a rear view of the humerus bone in conjunction with the bone scaffold in s stem of FIG. 11 depicting placement of a plate portion with respect to the humerus bone.
Figure 11B:
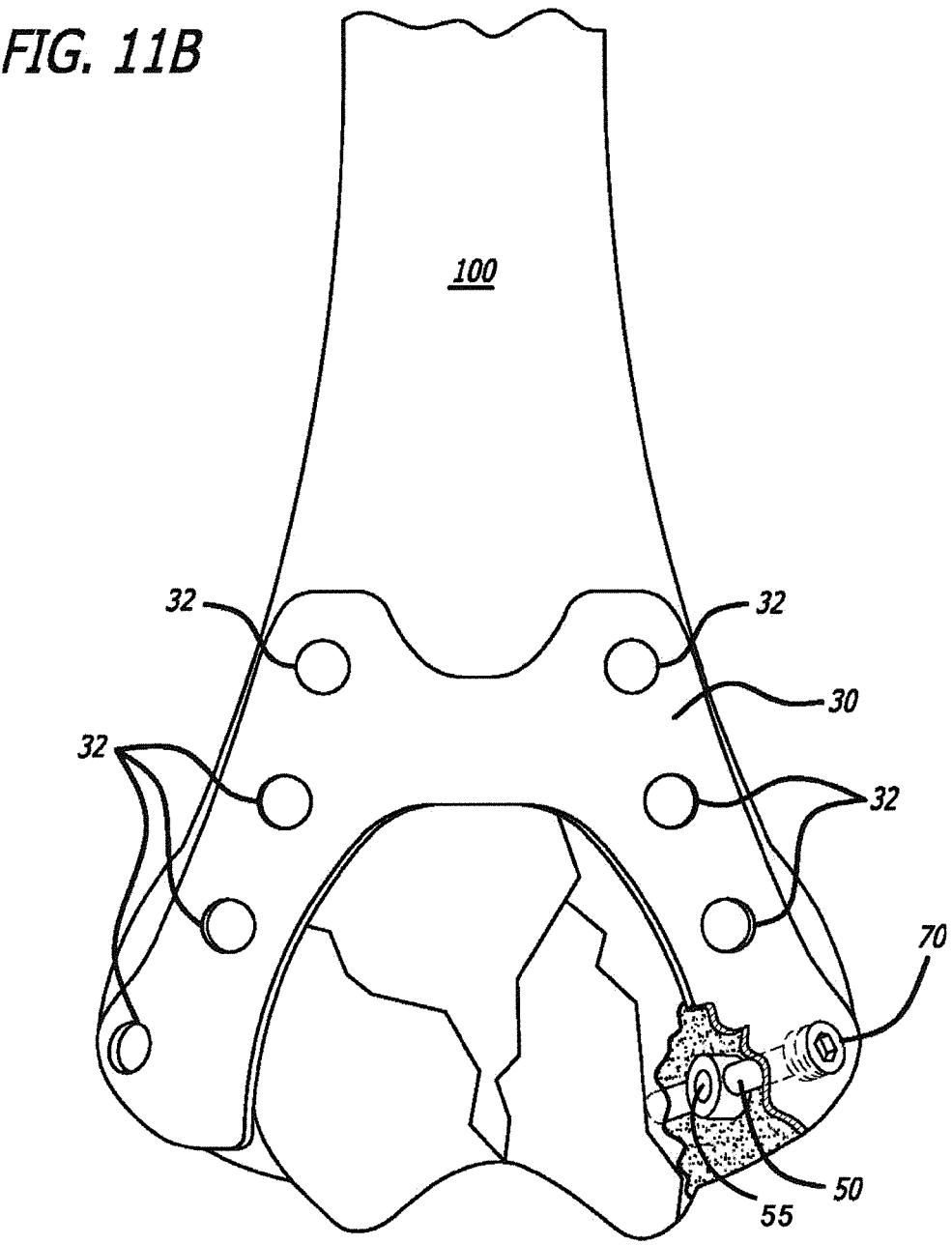
FIG 11Bis a rear partial cutaway view of the humerus bone in conjunction with the bone scaffolding system of FIG. 11 depicting placement of a scaffolding locking screw with regards to the plate portion and the humerus bone.

In an alternative embodiment of the present invention, a screw system is provided comprising a rod screw 60 configured for insertion into a scaffold locking screw 50 as illustrated FIGS. 11, 11A, and 11B. The scaffold locking screw 50 includes a threaded head 70, and will preferably be configured for insertion into the bone in such a manner as to permit a rod screw 60 to be cooperatively engaged an aperture 55 therein. Although FIG. 11 shows an exemplary embodiment wherein the rod screw 60 enters the scaffold locking screw 50 in a generally perpendicular manner, it will be appreciated by those skilled in the art that such a configuration is not required. In fact, any of a number of angular variations is possible and may be preferred depending upon specific circumstances surrounding a particular surgery. The rod screw 60 can be configured with threads 62 thereupon for secure engagement within the bone of a patient. Likewise, it may be desirable that the scaffold locking screw 50 include threads on an outer surface thereof to engage bone structure in a secure manner. The scaffold locking screw 50 may also include threads on an inner surface of the aperture 55 therein configured to securely engage cooperating threads on the outside circumference of the rod screw 60.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method for repairing a fractured bone, the method comprising:
   first, providing a bone fracture fixation assembly including a plate, an elongated shaft, and a rod, at least a portion of the shaft being threaded, the shaft having a hole extending therethrough, the hole having an axis transverse to a longitudinal axis of the shaft;
   second, extending the shaft into the bone and positioning the plate adjacent the surface of the fractured bone;
   third, directly engaging the threaded portion of the shaft with a screw receiving aperture of the plate;
   fourth, extending the rod into the bone; and
   fifth, inserting the rod into the hole of the shaft.

2. The method according to claim 1, wherein the hole of the shaft is threaded and the rod has a threaded portion adapted to threadably engage the hole of the shaft.

3. The method according to claim 1, wherein the axis of the hole is perpendicular to the longitudinal axis of the shaft.

4. The method according to claim 1, further comprising engaging another threaded portion of the shaft with the bone.

5. The method according to claim 1, further comprising contacting a non-threaded portion of the shaft with the bone.

6. The method according to claim 1, wherein the shaft is a locking screw.

7. The method according to claim 1, wherein the rod is a screw.

8. The method according to claim 1, further comprising engaging a threaded portion of the rod with the bone.

9. The method according to claim 1, further comprising contacting a non-threaded portion of the rod with the bone.

10. The method according to claim 1, wherein the rod has a non-threaded portion configured to fit within the hole of the shaft.

11. The method according to claim 1, wherein the rod has a length greater than the length of the shaft.

12. The method according to claim 1, wherein the rod has a shaft with a distal end and an opposite proximal end, at least a portion of the shaft of the rod being threaded.

13. The method according to claim 12, further comprising passing the distal end of the rod through to extend beyond the hole of the elongated shaft.

14. The method according to claim 1, wherein the plate includes a length and a width, the length being greater than the width, and the plate being curved along the length.

15. The method according to claim 1, wherein the shaft has a maximum width in a plane perpendicular to the longitudinal axis of the shaft, and the rod has a longitudinal axis and a maximum width in a plane perpendicular to the longitudinal axis of the rod, the maximum width of the shaft being greater than the maximum width of the rod.

* * * * *

UNITED STATES PATENT AND TRADEMARK OFFICE
CERTIFICATE OF CORRECTION

PATENT NO. : 8,361,075 B2
APPLICATION NO. : 12/803394
DATED : January 29, 2013
INVENTOR(S) : Eduardo Gonzalez-Hernandez It is certified that error appears in the above-identified patent and that said Letters Patent is hereby corrected as shown below:

<u>Title Page 2, References Cited, Item (56), Other Publications</u>:
Column 2, line 59: change "(cataiog)" to --(catalog)--;
Column 2, line 63: change "*J Bone Joint Surd*" to --*J Bone Joint Surg*--;
Column 2, line 64: change "et ai." to --et al.--;
Column 2, line 66: change "vol, 50," to --vol. 50,--;
Column 2, line 67: change "articie" to --article--; and change "3859:" to --3859;--; and
Column 2, line 68: change "voiume" to --volume--.

<u>Title Page 3, Item (56), Other Publications</u>:
Column 1, line 2: change "No,:" to --No.:--;
Column 1, line 8: change "Fixed-Angie" to --Fixed-Angle--; and
Column 2, line 1: change "instrument" to --Instrument--.

Signed and Sealed this
Third Day of September, 2013

Teresa Stanek Rea
*Acting Director of the United States Patent and Trademark Office*